United States Patent [19]

Dudzinski et al.

[11] Patent Number: 4,795,834

[45] Date of Patent: Jan. 3, 1989

[54] CATALYTIC ALKYLATION OF PRIMARY AND SECONDARY AMINO GROUPS IN LINEAR POLYAMINES

[75] Inventors: Zdzislaw Dudzinski, Clifton; Phillip Adams, Murray Hill, both of N.J.

[73] Assignee: Stepan Company, Northfield, Ill.

[21] Appl. No.: 20,394

[22] Filed: Mar. 2, 1987

[51] Int. Cl.$^4$ ............................................. C07C 85/06
[52] U.S. Cl. .................................... 564/479; 564/480
[58] Field of Search ................................ 564/479, 480

[56] References Cited

U.S. PATENT DOCUMENTS

| | | | |
|---|---|---|---|
| 3,373,204 | 3/1968 | Hales et al. | 564/480 |
| 4,153,581 | 5/1974 | Habermann | 564/479 |
| 4,404,404 | 9/1983 | Swift et al. | 564/480 |
| 4,594,455 | 6/1986 | Dudzinski | 564/479 |

*Primary Examiner*—Glennon H. Hollrah
*Assistant Examiner*—John A. Sopp
*Attorney, Agent, or Firm*—Andrew F. Zikas

[57] ABSTRACT

The catalytic alkylation of primary and secondary amino groups in linear polyamines using an "activated" copper catalyst.

9 Claims, No Drawings

CATALYTIC ALKYLATION OF PRIMARY AND SECONDARY AMINO GROUPS IN LINEAR POLYAMINES

This invention relates to the total or partial catalytic alkylation of amino groups in linear polyamines. More particularly, this invention relates to the catalytic alkylation with alcohols of linear polyamines such as triethylene tetramine and diethylene triamine, and, even more particularly, to the catalytic alkylation of linear polyamines with primary alcohols of from 6 to 20 carbon atoms, n-dodecanol being representative of such alcohols.

The classical method of alkylating amines is to treat the amine with an alkyl halide in the presence of a base. This reaction gives reasonable yields even for linear polyamines when the alkyl halide is of low molecular weight as for example methyl chloride or methyl bromide. But higher molecular weight alkyl halides, such as those having 6 or more carbon atoms, react sluggishly even with simple amines, and often partially decompose in the presence of linear polyamines at reaction temperatures.

A more recently developed method of alkylating amines in general is to treat them with alcohols in the presence of a catalyst. U.S. Pat. No. 4,594,455 provides a general description of this method, and it is, therefore, included herein by reference. This patent discloses that simple amines can be alkylated with high molecular weight alcohols using unsupported metal oxides together with nickel on kieselguhr as a catalyst.

Unfortunately, the use of a nickel catalyst causes disproportionation in amine alkylation. The use of catalysts containing copper oxide and a Group II metal without nickel may promote the alkylation of simple amines with alcohols but fails to achieve good yields of the intended products with linear polyamines. A main reason for the lack of success of copper containing catalysts in the alkylation of linear polyamines with alcohols is that the polyamine a "appears" to "poison" the catalyst.

An example of the above is the use of a very well known catalyst for alkylation of amines with alcohols comprising a mixture of copper oxide and the hydroxide of a Group II metal such as calcium hydroxide, barium hydroxide, or magnesium hydroxide with, the ratio of copper oxide to the hydroxide being from about 2 to 1, to about 6 to 1. When such a catalyst is used in the alkylation of triethylene tetramine or diethylene triamine, the polyamine appears to cause the catalyst to coagulate and settle to the bottom of the reactor in hard lumps or round balls, thereby halting the alkylation in the early stages of the reaction.

Since catalytic alkylation with alcohols is the commercially feasible method of alkylating amines, it is an object of the present invention to provide an improved method of catalytically alkylating linear polyamines with alcohols haing at least 6 carbon atoms, using mixtures of copper oxide and Group II metal hydroxides as catalyst, in such a manner as to prevent the poisoning of the catalyst by the polyamine.

It is another object of this invention to provide a method of pre-treating a catalyst comprising copper oxide and one or more Group II metal hydroxides in admixture in such manner that this catalyst would not be "poisoned" and thereby become inactive in the presence of a linear polyamine when it is to be alkylated catalytically by alcohols having at least 6 carbon atoms.

It has now been discovered, that a catalyst comprising copper oxide, and one or more Group II metal hydroxides may be pre-treated, or "activated" so that it is not poisoned by the linear polyamine, and therefore catalyzes the alkylation of the polyamine in good yields. The Group II metal hydroxide (or oxide) used in the catalyst system may, for example, be calcium, barium, magnesium hydroxide or mixtures thereof, with the ratio of copper moiety to Group II metal moiety preferably being in the range of about 2–6:1.

The pre-treatment, or "activation" comprises passing hydrogen gas into a suspension of the catalyst in the liquid alcohol that is to be the alkylating agent at a temperature of between about 200° C. to about 220° C. for a period of about 60 minutes or longer. When the catalyst is so "conditioned", or "activated", it is not poisoned by the subsequent addition of a linear polyamine.

The liquid alcohol that is to become the alkylating agent and the catalyst may be placed in a reactor fitted with an agitator, means for introducing hydrogen gas into the bottom of the reactor, means for recirculating the hydrogen gas, means for heating the contents of the reactor, and a condenser with a receiver adapted to distill the by-product, (water), out of the reaction mixture.

The contents of the reactor may be agitated while being heated, and hydrogen gas may be bubbled thereinto during the heating period. It generally requires about 60 minutes or more for the temperature to reach about 200° C. to 220° C. The heating is thereafter maintained at approximately that constant temperature while hydrogen is added for an additional period of about 15 to 45 minutes. This prereaction treatment "activates" the catalyst so that it is not poisoned by the subsequent addition of linear polyamines into the heterogeneous mixture of liquid alcohol and solid catalyst.

The amount of catalyst required for the alkylation of linear polyamines ranges from about ¼ of 1% to about 5% by weight, based on the weight of the alkylating alcohol. The rate of reaction is not necessarily proportional to the amount of catalyst used, but larger quantities of catalyst do increase the rate (in less than proportional amounts).

The mixture of "activated" catalyst is dispersed in the liquid alcohol and to it is added an "equivalent" quantity of linear polyamine. One equivalent weight of alcohol is one molecular weight of alcohol, while one equivalent weight of polyamine depends on the number of N-H groups whose alkylation is desired.

For example, the molecular weight of triethylene tetramine is 146, and it has 6 N-H bonds. If it is desired to alkylate all six N-H bonds, then the equivalent weight of for example, the polyamine becomes 146÷6, or 26.5 gms. Therefore, since the equivalent weight of n-dodecanol is 186, it would take at least 186 gm. of n-dodecanol to fully alkylate 26.5 gm. of triethylene tetramine. If a lower degree of alkylation is desired, then less n-dodecanol should be used.

By similar calculations, it would require at least 186 grams of n-dodecanol to fully alkylate 20.6 gm. of diethylene triamine which has a molecular weight of 103, five N-H bonds, and an equivalent weight of 20.6 gm.

Appears desirable to add the linear polyamine slowly to the alcohol in which the pre-treated catalyst is dispersed by the agitator because a larger concentration of unreacted polyamine may poison the catalyst.

The linear polyamine may be added dropwise, or in small discontinuous portions. The linear polyamine may also be dissolved in additional alkylating alcohol before being added since an excess of the alcohol does not reduce the effectiveness of the procedure but only adds to the number of equivalent weights of alcohol in the reaction mixture. A hydrogen-containing gas stream is preferable recirculated continuously into the reaction mixture while the linear polyamine is added. The addition of the polyamine takes place over varying periods depending on the compounds being used but is generally a period of about 2 to 6 hours.

After the addition of the polyamine is completed, the reaction mixture may be heated at the reaction temperature for an additional period (generally between about 2 to 4 hours) while hydrogen addition and agitation are continued. It was found that this additional heating, after complete addition of the polyamine, reduced the quantity of non-nitrogenous by-products in the reaction mixture.

The "activation" of the catalyst, and also the temperature of reaction may be conducted in the range of about 200° C. to about 220° C.

It was found that if the reaction temperature is 220° C., the reaction rate tends to be faster and the polyamine may be added at a slightly faster rate. The higher temperature of reaction also is preferred when it is desired to alkylate the polyamine as completely as possible, that is, to convert most of the amino groups to tertiary amino groups. On the other hand, at a reaction temperature of only 170° C., the reaction rate may be found to be too slow to be practical because even a slow addition of polyamine would often poison the catalyst.

At reaction temperatures of about 200° C. or above the final product contains non-nitrogenous impurities. The amount of these impurities increases if the reaction temperature is higher, and if the number of equivalents of alcohol is increased with respect to the polyamine. The average amount of these non-nitrogenous impurities in the final alkylation product usually is between about 5% and about 12% by weight relative to the weight of the alkylated polyamine.

It was found to be possible to convert almost all of the non-nitrogenous impurities into water soluble or volatile materials by hydrolysis. Therefore the mother liquors could be freed of these undesired impurities, after hydrolysis, by extraction with water and by volatization.

Since the impurities are mainly mixtures of high boiling esters and other condensation products which are hydrolyzable by aqueous alkali, the following method of purifying the mother liquors is suggested. All, or a portion, of the mother liquors can be heated with aqueous alkali for several hours, at which time almost all of the nonnitrogeneous matter is converted into water soluble or volatile products. The mixture, now comprising two layers, may be separated and the non-aqueous layer may be extracted several times with water, after which the residue may be heated under reduced pressure to volatilize the low-boiling impurities.

The following examples are illustrative of the present invention:

EXAMPLE 1

The purpose of this example is to alkylate catalytically trialkylene tetramine as fully as possible with n-dodecanol without using an excess of the alcohol and without extending the reaction time beyond one working day. Using an excess of alkylating alcohol is within the scope of this invention.

700 gm. (3.76 moles) of 98% n-dodecyl alcohol (n-dodecanol) liquid, 14.0 gm. of powdered copper oxide and 3.5 gm. of solid calcium hydroxide were placed in a one liter reactor which was provided with an agitator, means for introducing and recirculating hydrogen gas into the bottom of the reactor, means for heating the reactor, and means for distilling out volatile by-products, such as water, by using a condenser and receiver.

Hydrogen gas was bubbled into the receiver at a rate of 800 ml. per minute. (A preferred range for the rate of introduction of hydrogen into a 1 liter reactor is 400 ml. to 1 liter per minute).

The reaction mixture was heated slowly during agitation, while hydrogen was bubbled through it, until it reached a temperature of about 210° C. in about 60 minutes. At this point, the rate of heating was reduced so that the temperature of the contents remained approximately constant at about 210° C. With constant stirring, hydrogen gas was introduced into the reaction mixture for an additional 15 minutes, and the temperature reached 215° C. The temperature was now raised to 220° C., and while the reaction mixture was being stirred and while gas was being introduced, 92 gm. (0.63 moles) of triethylene tetramine was added at a rate of about 2.5 ml. to 3.0 ml. every 5 to 7 minutes so that the entire addition took about 3 hours. (It is to be noted that in this example the amount of catalyst was about 2% by weight of the n-dodecanol and that the ratio of copper oxide to calcium hydroxide was about 4 to 1. These are within the range of this invention).

Heating of the reaction mixture with agitation and hydrogen recirculation was continued at about 220° C. for 2½ additional hours.

The reaction mixture was cooled, washed with water to remove water-soluble materials, and then dried. The residue weighed 600 grams.

300 grams of residue (from the mother liquors) was mixed with a solution of 30 gm. of potassium hydroxide in 100 gm. of water and 100 gm. of isopropanol and the mixture was heated, while being stirred, at 83° C. for 5 hours.

The two resultant layers were separated, after which the aqueous layer was discarded and the non-aqueous layer was washed several times with water to extract the water soluble components.

This non-aqueous layer was dried and was then heated to 118°-120° C. at 4 mm. pressure in order to remove all volatile matter. About 12 gm. of volatile material distilled out. The residue weighed 250 gm.

The total number of primary, secondary and tertiary amine equivalents was determined by the standard method of determining amino nitrogen by titrating with standardized hydrochloric acid, in isopropanol, using bromocresol green indicator. The sum of the number of secondary and tertiary amine equivalents was determined by the method described in Organic Functional Group Analysis by F. E. Critchfield, International Series, Pergamon Press Book, The Macmillan Company, pp. 43-45.

The sum of the number of primary and secondary amine equivalents was determined by the method described in the above-named text at pp. 39-41.

From these three analyses it was determined that of all the amino nitrogen equivalents in the product, about 68.9% were tertiary amino groups, about 30.7% were secondary amino groups, and about 0.3% were primary amino groups. About 0.6% of the product was estimated to be non-nitrogenous material.

From the above results it was concluded that in triethylene tetramine ($H_2NC_2H_4NHC_2H_4NHC_2H_4NH_2$) the two terminal primary amino groups are the most easily alkylated by the method of the present invention, possibly because there is such a low quantity of primary amino nitrogens in the product.

Since only 50% of the crude mother liquors were purified, and this yielded 250 gm. of purified material, the yield would appear to be about 500 gm of purified material if all of the crude material had been purified.

In actual practice the yield would probably be even greater than 500 gm. because in the above example six 30 gm. samples were withdrawn from the reaction mixutre for analytical purposes before the procedure was concluded. It appears that the yield might also have been greater if the ratio of equivalents of alcohol to triethylene tetramine were greater than 1:1.

EXAMPLE 2

The procedure described in Example I was repeated, except that 65 gm. (0.63 moles) of diethylene triamine was used instead of 92 gm. (0.63 moles) of triethylene tetramine. Furthermore, the diethylenetriamine was dissolved in about 100 gm. of n-dodedanol before it was added to the reaction mixture. No samples of reaction mixture were withdrawn for analytical purposes.

The yield of alkylated diethylene triamine was 458 gm. Of the total number of amino equivalents in the product about 76.0% was tertiary amine, about 23.0% was secondary amine, and about 0.1% was primary amine. About 0.6% of the product was estimated to be non-nitrogenous material.

EXAMPLE 3

The procedure described in Example 1 was repeated, except that instead of n-dodecanol, a commercial mixture of normal alcohols containing 0.4% of n-hexanol, 42.0% of n-octanol, 57.1% of n-decanol, and 0.5% of normal alcohols containing more than 12 carbon atoms was used. 550 grams of this mixture represented about 3.8 moles of alcohol, and this quantity was used instead of 3.76 moles of n-dodecanol. In addition, the 92 gm. of triethylene tetramine was dissolved in about 100 gm. of the alcohol mixture before being added to the reaction mixture.

The yield of alkylated triethylene tetramine was 500 gm. About 77.1% of the amino groups in the product were tertiary amino groups, about 22.5% were secondary amino groups and about 0.4% were primary amino groups.

The products of this invention are used, among other things, as intermediates in the synthesis of quaternary ammonium salts which have anti-microbial properties. Furthermore, since they are substantive to textiles, they are especially adapted for products used in this field.

As is apparent from the foregoing specifications, the invention is susceptible of being embodied with various alterations and modifications which may differ particularly from those that have been described. Accordingly, it is to be fully understood that all of the foregoing is intended to be merely illustrative, and it is not to be construed or interpreted as being restrictive or otherwise limiting of the instant invention, excepting as it is set forth and defined in the hereto-appended claims.

The invention claimed is:

1. A method of catalytically aminating at least one alcohol with at least one linear polyamine, comprising:
   activating a catalyst system comprised of a mixture of copper oxide and at least one Group II metal hydroxide by dispersing said catalyst system in said alcohol and heating the resulting dispersion at a temperature between about 200° to 220° C. while passing a gas stream comprised of hydrogen therethrough;
   adding a select amount of said linear polyamine to said alcohol containing the activated catalyst system therein so that a reaction occurs; and
   purifying the resultant reaction product.

2. The method of claim 1 wherein the reaction product is substantially purified of non-nitrogenous impurities by converting said impurities into water-soluble or volatile materials by hydrolysis and then extracting said impuriites by extraction with water and by volatization.

3. The method of claim 2 wherein the hydrolysis is effected by heating the mother liquors of the reaction with aqueous alkali until substantially all of the non-nitrogenous impurities are converted into water-soluble or volatile materials, forming aqueous and non-aqueous layers, then separating the aqueous from the non-aqueous layer and extracting the non-aqueous layer with water, and thereafter heating the residue to volatilize any low-boiling impurities.

4. The method of claim 1 wherein the amount of catalyst is between about 0.25 to about 5.0% by weight, based on the weight of the alkylating alcohol.

5. The method of claim 1 wherein the alcohol is a primary alcohol of from 6 to 20 carbon atoms.

6. The method of claim 1 wherein the linear polyamine is selected from the group consisting of triethylene tetramine and diethylene triamine.

7. The method of claim 1 wherein said adding of the linear polyamine to said alcohol occurs at a temperature between about 200° to about 220° C.

8. The method of claim 1 wherein the alcohol is n-dodecyl alcohol.

9. The method of claim 1 wherein the alcohol is a primary alcohol of from 6 to 12 carbon atoms.

* * * * *